(12) United States Patent
Ludescher et al.

(10) Patent No.: US 6,284,888 B1
(45) Date of Patent: Sep. 4, 2001

(54) VINYL-ACA PURIFICATION PROCESS

(75) Inventors: Johannes Ludescher, Breitenbach; Werner Veit, Kufstein, both of (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/567,623

(22) Filed: May 9, 2000

Related U.S. Application Data

(63) Continuation of application No. 09/011,338, filed as application No. PCT/EP96/03582 on Aug. 13, 1996, now abandoned.

(30) Foreign Application Priority Data

Aug. 14, 1995 (AT) ........................................ 1369/95

(51) Int. Cl.⁷ ....................... C07D 501/12; C07D 501/22
(52) U.S. Cl. ........................................... 540/220; 540/215
(58) Field of Search .................................... 540/215, 220

(56) References Cited

FOREIGN PATENT DOCUMENTS

| A 0 503 453 | 9/1992 | (EP) . |
|---|---|---|
| A 0 597 429 | 5/1994 | (EP) . |
| WO A 93 16084 | 8/1993 | (WO) . |

*Primary Examiner*—Mark L. Berch
(74) *Attorney, Agent, or Firm*—Lydia T. McNally

(57) ABSTRACT

A process for purification of vinyl-ACA of formula

I

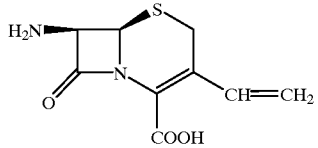

from a mixture of vinyl-ACA and 7-ADCA of formula

II

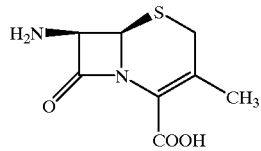

is provided. The process comprises a) producing a mixture of a salt of vinyl-ACA and a salt of 7-ADCA in a solvent in which the salt of 7-ADCA has a higher solubility than the salt of vinyl-ACA, and b) subjecting the mixture to crystallization to obtain a precipitate of the salt of vinyl-ACA. A process of purifying vinyl-ACA from a mixture of vinyl-ACA and 7-ADCA via chromatography, particularly adsorption chromatography is also provided.

12 Claims, No Drawings

VINYL-ACA PURIFICATION PROCESS

This application is a continuation of U.S. application Ser. No. 09/011,388, now abandoned having a 35 USC 371 date of Apr. 20, 1998, which application is a 371 of International Application No. PCT/EP96/03582 filed Aug. 13, 1996.

The present invention relates to a process for the purification of vinyl-ACA in a mixture of vinyl-ACA and 7-ADCA, by depletion of 7-ADCA in a mixture of vinyl-ACA and 7-ADCA.

Vinyl-ACA of formula

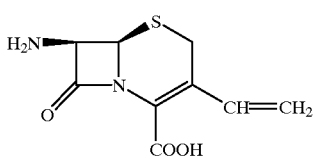

I may be used as intermediate in the production of highly active, oral antibiotics, e.g. cefixime and cefdinir of formulae

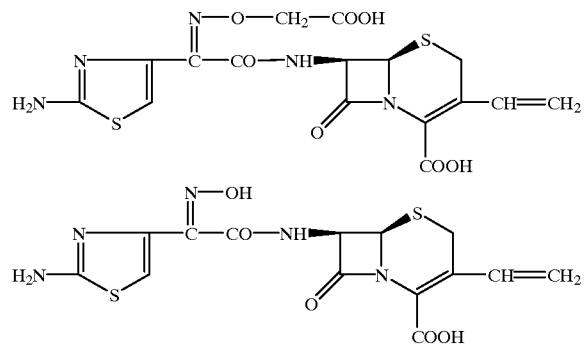

Vinyl-ACA may be produced, for example, by Wittig reaction of a corresponding cephalosporin-3-ylide, which may have the amine group and the carboxylic acid attached to the ring system protected, with formaldehyde (see e.g. Journal of Antibiotics, Vol. 38, No. 12, 1739 ff; or EP-0 503 453; or EP-0 597 429). We have found that such vinyl-ACA may be contaminated, e.g. by 7-ADCA. This is consistent with the fact that phosphine alkylenes (ylides) or quaternary phosphonium compounds can hydrolyze to form the corresponding alkane and phosphine oxide (see e.g. Houben Weyl, Methoden der organischen Chemie, Phosphorverbindungen I, volume 12/1, especially pages 108 and 119). We found accordingly, when producing a compound of formula I via a Wittig reaction, as a by-product 7-ADCA of formula

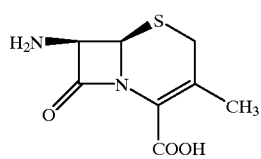

II or a protected derivative thereof may be formed. Furthermore, if 7-ACA is produced via fermentative production of cephalosporin C and subsequent conversion to 7-ACA, the thus formed 7-ACA may contain 7-ADCA, because the 7-ADCA-analogous cephalosporin is formed in the course of fermentation, or is not wholly metabolised to cephalosporin C. Thus, 7-ACA, used for example as a starting material for 7-ACA, may often have an undesired 7-ADCA content, for example of more than 1%.

In the production of active cephalosporins, e.g. cefixime and cefdinir, wherein an intermediate of formula I may be used, the 7-ADCA content in vinyl-ACA of formula I should be as low as possible, because upon appropriate further substitution of a compound of formula I, 7-ADCA could react in the same way as vinyl-ACA which would result in contamination of the desired active vinyl-ACA compounds, e.g. cefixime or cefdinir, by analoguously substituted 7-ADCA-compounds, which are difficult to separate.

According to the present invention, vinyl-ACA in a mixture of vinyl-ACA and 7-ADCA can be purified in an economical manner by depletion of 7-ADCA to, e.g. less than 0.1% to 0.8%, such as less than 0.1% to 0.6%, for example 0.3% to 0.8%. This is remarkable, because 7-ADCA and vinyl-ACA are chemically very similar compounds.

In one aspect the present invention provides a process for the depletion of 7-ADCA of formula II in a mixture of 7-ADCA and vinyl-ACA of formula I, preferably by a process,
wherein
a) a mixture of a salt of a compound of formula I and a compound of formula II is subjected to crystallization, the crystallized salt is isolated and converted into a compound of formula I, containing less compound of formula II than the mixture of a compound of formula I and formula II, or
b) a mixture of a compound of formula I and a compound of formula II is subjected to chromatography.

The salt includes for example a cationic salt of the carboxylic acid group and an amine salt of the carboxylic acid group in a compound of formulae I and II.

In a further aspect the present invention provides a process as described above, wherein a mixture of a salt of a compound of formula I and a compound of formula II is a mixture of compounds of formulae

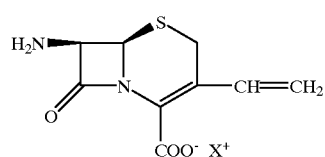

III

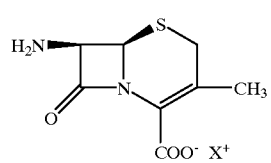

IV wherein $X^+$ denotes a cation, or a compound of formula

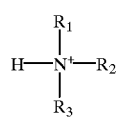

V wherein $R_1$, $R_2$ and $R_3$ are the same or different and independently of one another denote hydrogen, alkyl, aryl, aralkyl, or cycloalkyl; or $R_1$ and $R_2$ together with the nitrogen atom form a heterocycle and $R_3$ is as defined above.

The cation includes a cation of the alkali series, for example $Li^+$, $K^+$, $Na^+$.

Preferably $R_1$ denotes hydrogen and $R_2$ and $R_3$ independently from one another denote alkyl or aralkyl. $R_1$ and $R_2$ together with the nitrogen atom may denote a heterocycle, preferably a 5- or 6 membered heterocycle, having for example 1 to 3 heteroatoms.

If not otherwise defined herein, any carbon containing radical contains up to 10 carbon atoms. Alkyl includes straight chain or branched $C_{1-22}$alkyl, preferably $C_{1-12}$alkyl, such as $C_{1-8}$alkyl. Aryl includes unsubstituted aryl or substituted aryl, preferably phenyl or, mono- or polysubstituted phenyl. Aralkyl includes unsubstituted aralkyl, or substituted aralkyl, for example benzyl. Cycloalkyl includes $C_{3-8}$cycloalkyl, such as $C_{3-6}$cycloalkyl. A heterocycle includes unsubstituted heterocycle or substituted heterocycle, for example 5- or 6-membered heterocycle. A heterocycle may contain one or several heteroatoms, for example N, S, O. Substituents of any aryl group, aralkyl group and of any heterocycle include substitutents which are inert under the corresponding reaction conditions, for example alkyl, aryl, alkoxy, aryloxy, halogen, nitro, optionally protected amine groups, optionally protected hydroxy.

Process variant a) may be carried out as follows:

A salt of a mixture of a compound of formula I and of formula II may be produced, for example, by adding a salt forming agent to a mixture of a 7-ADCA and vinyl-ACA in a solvent. A salt forming agent includes, for example, a base. A base includes, e.g. an inorganic base, e.g. a hydroxide, for example an alkali hydroxide; and a salt having a cation source; such as an inorganic salt, for example an alkali salt, such as a carbonate, hydrogencarbonate; and an organic salt, for example the salt of a carboxylic acid, for example an alkali salt, of, for example acetic acid or 2-ethylhexanoic acid; and an organic base, for example a nitrogen base, for example ammonia or an amine, for example an amine of formula

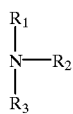

VI wherein $R_1$, $R_2$ and $R_3$ are as defined above.

In a further aspect the present invention provides a process as described above, wherein a mixture of a salt of a compound of formula I and a compound of formula II is produced by addition of a salt forming agent to a mixture of a compound of formula I as defined in claim 1 and a compound of formula II as defined in claim 1 in a solvent, preferably a process, wherein the salt forming agent is an inorganic base, an inorganic salt, an organic salt or a nitrogen base; preferably, the inorganic base is a hydroxide; the inorganic salt is an inorganic alkali salt; the organic salt is an alkali salt of a carboxylic acid; and the nitrogen base is a compound of formula

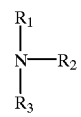

VI wherein $R_1$, $R_2$ and $R_3$ are as defined above.

A solvent includes an aprotic solvent and a protic solvent, for example an amide, such as N,N-dimethylform-amide, a ketone, such as acetone; an alcohol, such as methanol, ethanol or one of the isomeric propanols or butanols, for example isopropanol; a nitrile such as acetonitrile; ethers or chlorinated hydrocarbons; water; and mixtures of solvents.

In one aspect a mixture of vinyl-ACA and 7-ADCA may be dissolved in water or in an aqueous organic solvent, for example a mixture of water and a ketone; and a mixture of water and an alcohol, such as ethanol or isopropanol; in the presence of a salt forming agent. The pH may be appropriately adjusted, for example by addition of a base, having, for example, a Li, Na or K-source, such as an acetate; particularly in case that an organic base, such as a nitrogen base is used as salt forming agent. An anti-solvent, for example a nitrile, such as acetonitrile; an alcohol such as methanol, ethanol or one of the isomeric propanols or butanols; an ether, such as diethyl ether, tetrahydrofuran or tertbutylmethyl ether; a ketone, such as acetone; or an ester, such as ethyl acetate or acetic acid isopropyl ester; or mixtures of anti-solvent; may be added. The salt of vinyl-ACA, or a mixture of a salt of vinyl-ACA and 7-ADCA, wherein the 7-ADCA content is less than in the mixture used for salt production, may crystallize.

In another aspect a mixture of vinyl-ACA and 7-ADCA may be suspended in a practically water-free organic solvent, such as an amide, a ketone; an alcohol; a nitrile; an ether; a chlorinated hydrocarbon; and mixtures of water-free organic solvent. Preferred solvent include a mixture of methanol with a ketone or a higher alcohol. A nitrogen base, for example of formula VI, and an anti-solvent as defined above may be added.

Surprisingly the undesired salt of 7-ADCA may be better soluble than the desired salt of vinyl-ACA and a salt of vinyl-ACA or a mixture of a salt of vinyl-ACA and 7-ADCA in which the content of 7-ADCA is less than in the mixture used for salt production is precipitated. By isolation of the precipitate which may be carried out as conventional, separation of a compound of formula III and of a compound of formula IV may be effected.

If required, process variant a) may be repeated with a product obtained according to 7 process variant a) resulting in further depletion of the undesired compound of formula II. A mixture of a salt of vinyl-ACA and 7-ADCA obtained may be resuspended in the solvent system in which crystallization had been carried out, and the solubility product may be adjusted, for example by addition of solvent or anti-solvent as appropriate, with the effect of further depletion of 7-ADCA.

A compound of formula III in crystalline form is new.

In another aspect the present invention provides a compound of formula

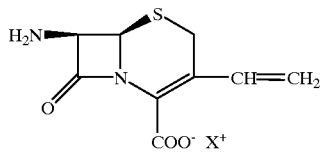

wherein X⁺ is as defined above, in crystalline form.

In another aspect the present invention provides the dicyclohexylammonium salt of 7-amino-3-vinyl-cephalosporanic acid in crystalline form;

tertoctylammonium salt of 7-amino-3-vinyl-cephalosporanic acid in crystalline form;

N-benzyl-tertbutylammonium salt of 7-amino-3-vinyl-cephalosporanic acid in crystalline form;

2-ethyl-1-hexylammonium salt of 7-amino-3-vinyl-cephalosporanic acid in crystalline form;

potassium salt of 7-amino-3-vinyl-cephalosporanic acid in crystalline form.

The salt of vinyl-ACA or of the mixture of vinyl-ACA and 7-ADCA may be isolated and converted into the free compound of formula I and formula II as conventional, for example by treatment with an acid, such as an inorganic acid, such as hydrochloric acid, sulphuric acid, preferably sulphuric acid; or an organic acid such as an organic carboxylic acid.

Process variant b) according to the present invention may be carried out as follows: Chromatography preferably may be adsorption chromatography. A mixture of vinyl-ACA and 7-ADCA may be dissolved, for example in water, for example in the presence of a base, e.g. ammonia. This solution is subjected to chromatography using an adsorbent. An adsorbent includes activated charcoal, e.g. Norit CG-1 or Cecarbon GAC 40; or an adsorber resin, such as styrene-divinylbenzene copolymerisates, for example Dianion HP 20 (CAS No.55353-13-4), Dianion HP 21 (Cas No. 92529-04-9) or Dianion SP 207 (CAS No. 98225-81-1) from Mitsubishi Kasei Corporation; Amberlite XAD 1180 (CAS No. 97396-56-0), Amberlite XAD 1600 (CAS No. 153796-66-8) or Amberlite XAD 16 (CAS No. 102419-63-8) from Rohm and Haas or Amberchrom CG 161 (CAS No. 131688-63-6) from TosoHaas; preferably CG 161 and XAD-1600. Elution may be carried out with water. The compound which elutes earliest may be in general 7-ADCA. Thus, fractions of the compound of formula II, mixtures of the compound of formula I and II and the pure compound of formula I may be obtained. Isolation of a compound of formula I may be carried out by adjustment of the pH of a fraction containing a compound of formula I obtained by the present invention to around the isoelectric point of a compound of formula I, for example as conventional, e.g. by addition of an acid, such as an inorganic acid, for example hydrochloric acid. The compound of formula I may crystallize.

Process variant b) is very simple to carry out. Elution may be effected with a purely aqueous medium, no organic solvent is to be used. The equipment required is simple. We have found that there is no need for elution by means of a gradient, nor step-wise elution, nor pH changes in the course of chromatographic purification. Process variant a) can be combined with process variant b) for still more effective depletion of 7-ADCA in a mixture of vinyl-ACA and 7-ADCA.

In another aspect the present invention provides the use of a compound of formula

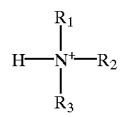

wherein X⁺ is as defined above, or the use of a process for the depletion of 7-ADCA of formula II in a mixture of 7-ADCA and vinyl-ACA of formula I, in the production of highly active cephalosporins, for example cefixime and cefdinir.

Processes a) and b) of the present invention represent very economical methods of separating 7-ADCA from mixtures of vinyl-ACA with 7-ADCA, which are very simple to carry out and which are suitable for use on industrial scale.

In another aspect the present invention provides a depletion process of 7-ADCA of formula

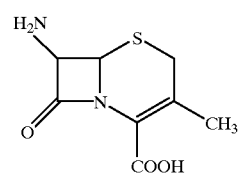

in mixtures of vinyl-ACA of formula

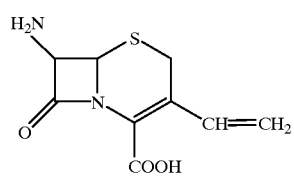

with 7-ADCA, characterized in that a) a mixture of vinyl-ACA and 7-ADCA is converted into salts of formula

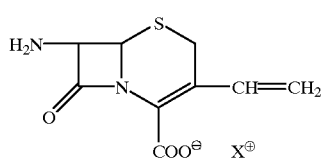

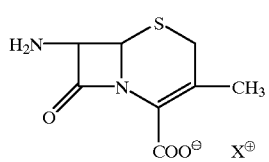

wherein $X^\oplus$ is $Li^\oplus$, $Na^\oplus$, $K^\oplus$ or a cation of formula

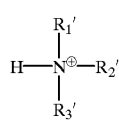
V wherein $R_1'$, $R_2'$ and $R_3'$ are the same or different and independently of one another denote hydrogen, $(C_{1-8})$ alkyl, optionally substituted benzyl or phenyl or $(C_{4-8})$ cycloalkyl, or $R_1'$ and $R_2'$ together with the nitrogen form a 5- or 6-membered heterocycle which optionally contains a further one or two hetero atoms, and $R_3'$ is as defined above, by reaction of the mixture of vinyl-ACA and 7-ADCA with a lithium, sodium or potassium base or with an amine of formula

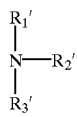
VI wherein $R_1'$, $R_2'$ and $R_3'$ are as defined above, whereby
α) the reaction is carried out in a solvent or solvent mixture in which the salts of formulae III and IV have different solubilities, or
β) the salts of the compounds of formulae III and IV are suspended in a solvent or solvent mixture, and the solubility product is adjusted, and after isolating the compound of formula III, this is converted using an acid into the compound of formula I having no content or a reduced content of 7-ADCA, or
b) a solution of a mixture of vinyl-ACA with 7-ADCA is chromatographed.

In the following examples all temperatures are given in degrees celsius.
The following abbreviations are used:

| | |
|---|---|
| Vinyl-ACA: | Compound of formula I |
| 7-ADCA: | Compound of formula II |
| GC: | Gas chromatography |
| KF: | Karl Fischer |
| HPLC: | High performance liquid chromatography |

EXAMPLE 1

Purification of Vinyl-ACA via the Dicyclohexylammonium Salt

1a) Dicyclohexylammonium Salt of Vinyl-ACA 12.7 g of vinyl-ACA, containing 1.1% 7-ADCA (HPLC), are suspended in a mixture of 56.5 ml of acetone and 3.75 ml of water. 12 ml of dicyclohexylamine are added in one portion. The mixture is stirred for ca. 5 minutes. A solution is obtained, stirring is stopped, and the solution is left to stand for ca. 15 minutes. Crystallization starts. The crystal mass is agitated. 115 ml of acetone are added dropwise within ca. 30 minutes. The reaction mixture is stirred for 2 hours at −10°, the crystalline precipitate is isolated, washed with acetone, and dried.

19.3 g of the dicyclohexylammonium salt of vinyl-ACA are obtained in crystalline form.

Analysis:

| | | |
|---|---|---|
| Vinyl-ACA | 48.4% | (HPLC) |
| 7-ADCA | 0.3% | (HPLC) |
| Dicyclohexylamine | 37.7% | (GC) |
| Acetone | 10.2% | (GC) |
| $H_2O$ | 3.7% | (KF) |

$^1$H-NMR ($D_2O$, trimethylsilylpropionic acid sodium salt-$d_4$): 6.71 (dd, J=11 and 18, C=CH); 5.40 (d, J=18, C=CH$_2$); 5.22 (d, J=11, C=CH$_2$); 5.07 (d, J=5, H$_7$); 4.75 (d, J=5, H$_6$); 3.70 (d, J=17, H$_2$); 3.56 (d, J=17, H$_2$); 3.12–3.70 (m); 2.00 (br); 1.79 (br); 1.65 (m); 1.00–1.34 (m).

1b) Dicyclohexylammonium Salt of Vinyl-ACA 2.26 g of vinyl-ACA, containing 0.5% of 7-ADCA, are suspended in a mixture of 11.3 ml of acetone and 1 ml of water. 2.4 ml of dicyclohexylamine are added under stirring and a solution is obtained. Crystallization starts, stirring is stopped and the resultant suspension is left to stand for 10 minutes. The crystal mass is agitated and 22.6 ml of acetone are added dropwise within ca. 10 minutes. The suspension is stirred for 30 minutes at room temperature, the precipitate is filtered off, washed with acetone, and dried.

3.0 g of the dicyclohexylammonium salt of vinyl-ACA are obtained in crystalline form.

Analysis:

| | | |
|---|---|---|
| Vinyl-ACA | 52.4% | (HPLC) |
| 7-ADCA | 0.2% | (HPLC) |
| Dicyclohexylamine | 39.6% | (GC) |
| Acetone | 3.6% | (GC) |
| $H_2O$ | 0.7% | (KF) |

1c) Vinyl-ACA via Dicyclohexylammonium Salt of Vinyl-ACA 8.15 g of the dicyclohexylammonium salt of vinyl-ACA, obtained as described in Example 1a), are dissolved in 160 ml of water at room temperature. The solution is stirred for 10 minutes with 0.8 g of activated charcoal. The charcoal is filtered off and the filter washed with 25 ml of water. The filtrate is adjusted to pH 3.4 with 10 N $H_2SO_4$ at room temperature within ca. 15 minutes. Precipitation occurs. The suspension is stirred for 1 hour whilst cooling with ice, the precipitate is isolated through a suction filter, washed with 3×10 ml of water and 3×10 ml of acetone and dried.

3.9 g of vinyl-ACA, containing 0.5% 7-ADCA, are obtained.

EXAMPLE 2

Purification of Vinyl-ACA via the Tert.octylammonium Salt of Vinyl-ACA

2a) Tert.octylammonium Salt of Vinyl-ACA 12.7 g of vinyl-ACA, containing 1.1% 7-ADCA, are suspended in a mixture of 56.5 ml of acetone and 56.5 ml of water. 10 ml of tert.octylamine are added in one portion. A solution is obtained within ca. 5 minutes. 226 ml of acetone are added. Stirring is stopped. Crystallization occurs. After ca. 15 minutes, the crystal mass is agitated, and 400 ml of acetone are added dropwise within ca. 30 minutes. The suspension is stirred for 2 hours whilst cooling with ice, the precipitate is isolated, washed with 50 ml of acetone and dried.

18.9 g of the tert.octylammonium salt of vinyl-ACA are obtained in crystalline form.

Analysis:

| | | |
|---|---|---|
| Vinyl-ACA | 56.8% | (HPLC) |
| 7-ADCA | 0.5% | (HPLC) |
| Tert.octylamine | 30.6% | (GC) |
| Acetone | 8.4% | (GC) |
| $H_2O$ | 3.3% | (GC) |

$^1$H-NMR (methanol-$d_4$, $D_2O$): 6.91 (dd, J=11 and 18, C=CH); 5.31 (d, J=18, C=$CH_2$); 5.11 (d, J=11, C=$CH_2$); 5.01 (d, J=5, br, $H_7$); 4.67 (d, J=5, br, $H_6$); 3.65 (d, J=17, $H_2$); 3.52 (d, J=17, $H_2$); 1.66 (s, $CH_2$); 1.43 (s, $CH_3$); 1.05 (s, $CH_3$).

2b Tert.octylammonium Salt of Vinyl-ACA 2.26 g of vinyl-ACA, containing 0.8% of 7-ADCA, are suspended in a mixture of 11.3 ml of acetone and 11.3 ml of water. 2 ml of tert.octylamine are added and a solution is obtained. 22.6 ml of acetone are added in one portion, and the mixture is left to stand for 10 minutes. Crystallization occurs. The crystal mass is agitated and mixed with a further 22.6 ml of acetone. The suspension is stirred for ca. further 30 minutes at room temperature, the precipitate is isolated and washed twice, each time with 10 ml of acetone. The product is dried.

3.0 g of the tert.octylammonium salt of vinyl-ACA are obtained in crystalline form.

Analysis:

| | | |
|---|---|---|
| Vinyl-ACA | 57.1% | (HPLC) |
| 7-ADCA | 0.3% | (HPLC) |
| Tert.octylamin | 31.0% | (GC) |
| Acetone | 5.8% | (GC) |
| $H_2O$ | 2.1% | (KF) |

2c) Vinyl-ACA via the Tert.octylammonium Salt of Vinyl-ACA 7.11 g of the tert.octylammonium salt of vinyl-ACA, obtained as described in Example 2a), are dissolved in 280 ml of water at 35° and stirred for 10 minutes with 0.7 g of activated charcoal. The charcoal is filtered off and the filter washed with 25 ml of water. The filtrate is cooled to 5° with ice water, and a pH of 3.4 is adjusted with 10 N $H_2SO_4$ within 15 minutes. The resultant suspension is stirred for ca. 30 minutes whilst cooling with ice, the precipitate is isolated, washed with 3×10 ml of water and 3×10 ml of acetone and dried.

4.0 g of vinyl-ACA, containing 0.8% of 7-ADCA, are obtained.

EXAMPLE 3

Purification of Vinyl-ACA via the Potassium Salt of Vinyl-ACA

3a) Potassium Salt of Vinyl-ACA 10 g vinyl-ACA, containing 1.0% of 7-ADCA (HPLC), are suspended in a mixture of 40 ml of 95% ethanol and 5 ml of water, and the suspension is cooled with ice water. 8.0 ml of triethylamine are added dropwise whilst stirring, the resultant solution is filtered and the filtrate is mixed with a solution of 10 g of potassium acetate in 15 ml of ethanol. Crystallization occurs. The crystal mass is agitated, and stirred for 15 minutes whilst cooling with ice. The precipitate is isolated by filtration, washed with ethanol and dried.

6.7 g of the potassium salt of vinyl-ACA are obtained in crystalline form.

Analysis

| | | |
|---|---|---|
| Vinyl-ACA | 78.7% | (HPLC) |
| 7-ADCA | 0.4% | (HPLC) |
| EtOH | 0.7% | (GC) |
| $H_2O$ | 1.8% | (KF) |

3b Potassium Salt of Vinyl-ACA 3 g of the potassium salt of vinyl-ACA, containing 0.4% of the potassium salt of 7-ADCA, obtained according to example 3a), are dissolved in 50 ml of water. 0.3 g of activated charcoal are added and the mixture is stirred for ca. 10 minutes at room temperature. The charcoal is filtered off, and the filter washed with 10 ml of water. The filtrate is cooled to 5°. The pH is adjusted to 3.4 with 10 N $H_2SO_4$ within ca. 15 minutes. After stirring for 1 hour whilst cooling with ice, the precipitate is isolated, washed 3× with 10 ml of water and 3× with 10 ml of acetone, and dried.

2.38 g of the potassium salt of vinyl-ACA, containing 0.3% of the potassium salt of 7-ADCA, are obtained in crystalline form.

EXAMPLE 4

Purification of Vinyl-A CA via the N-benzyl-tert.butylammonium Salt of Vinyl-ACA 4a) N-benzyl-tert.butylammonium Salt of Vinyl-ACA 5.13 g of vinyl-ACA, containing 1.0% of 7-ADCA, are suspended in a mixture of 22.6 ml of acetone and 6 ml of water. 5 ml of N-benzyl-tert.butylamine are added in one portion. A solution is obtained for a short time and crystallization occurs. The crystal suspension is left to stand for 15 minutes, the crystal mass is agitated, and 200 ml of acetone are added dropwise within ca. 30 minutes. The suspension is stirred for a further ca. 105 minutes whilst cooling with ice, the precipitate is isolated, washed with acetone, and dried. 3.2 g of the N-benzyl-tert.butylammonium salt of vinyl-ACA are obtained in crystalline form.

Analysis

| | | |
|---|---|---|
| Vinyl-ACA | 51.3% | (HPLC) |
| 7-ADCA | 0.2% | (HPLC) |
| N-benzyl-tert.-butylamine | 40.4% | (GC) |
| Acetone | 7.0% | (GC) |
| $H_2O$ | 2.0% | (KF) |

$^1$HNMR ($D_2O$, trimethylsilylpropionic acid sodium salt-$d_4$): 6.70 (dd, J=11 and 18, C=CH); 5.37 (d, J=18, C=$CH_2$); 5.20 (d, J=11, C=$CH_2$); 5.02 (d, J=5, $H_7$); 4.69 (d, J=5, $H_6$); 3.67 (d, J=17, $H_2$); 3.53 (d, J=17, $H_2$); 7.6 (m, ArH); 4.19 (s, $CH_2$); 1.42 (s, $CH_3$).

4b) Vinyl-ACA via the N-benzyl-tert.butylammonium Salt of Vinyl-ACA 2 g of the N-benzyl-tert.butylammonium salt of vinyl-ACA, obtained as described in Example 4a), are dissolved in 30 ml of water, and the solution stirred for 10 minutes at room temperature with 0.2 g of activated charcoal. The charcoal is filtered off and the filter washed with 10 ml of water. The filtrate is cooled to 5°. The pH is adjusted to 3.4 with 10 N $H_2SO_4$ within ca. 15 minutes. The suspension is stirred for a further 2 hours whilst cooling with ice, the precipitate is isolated, washed water and acetone, and dried.

1.03 g of vinyl-ACA, containing 0.3% (HPLC) of 7-ADCA, are obtained.

EXAMPLE 5

Purification of Vinyl-ACA via the 2-ethyl-1-hexylammonium Salt of Vinyl-ACA 5a) 2-Ethyl-1-hexylammonium Salt of Vinyl-ACA 5.13 g of vinyl-ACA, containing 1.0% 7-ADCA, are suspended in a mixture of 22.6 ml of acetone and 4 ml of water, and 4.7 ml of 2-ethyl-1-hexylamine are added in one portion. A solution is obtained within ca. 5 minutes. 200 ml of acetone are added dropwise whilst stirring. The resultant suspension is slowly stirred for 17 hours at −10°. The precipitate is isolated, washed with acetone which has been cooled to −10°, and dried. 4.4 g of 2-ethyl-1-hexylammonium salt of vinyl-ACA are obtained in crystalline form.

Analysis:

| Vinyl-ACA | 55.9% | (HPLC) |
|---|---|---|
| 7-ADCA | 0.3% | (HPLC) |
| 2-Ethyl-1-hexylamine | 31.8% | (GC) |
| Acetone | 11.1% | (GC) |
| $H_2O$ | 0.6% | (KF) |

$^1$H-NMR ($D_2O$, trimethylsilylpropionic acid sodium salt-$d_4$): 6.72 (dd, J=11 and 18, C=CH); 5.39 (d, J=18, C=CH$_2$); 5.22 (d, J=11, C=CH$_2$); 5.05 (d, J=5, H$_7$); 4.72 (d, J=5, H$_6$); 3.70 (d, J=17, H$_2$); 3.56 (d, J=17, H$_2$); 2.91 (d, J=6, CH$_2$N); 1.60–1.70 (m, CH); 1.20–1.40 (m, CH$_2$); 0.85 (2xt, J=7, CH$_3$).

5b Vinyl-ACA via 2-ethyl-1-hexylammonium Salt of Vinyl-ACA 2.5 g of the 2-ethyl-1-hexylammonium salt of vinyl-ACA, obtained as described in Example 5a), are dissolved in 40 ml of water and stirred for 10 minutes at room temperature with 0.25 g of activated charcoal. The charcoal is filtered off and the filter washed with 10 ml of water. The filtrate is cooled to 5°. The pH is adjusted to 3.4 with 10 N $H_2SO_4$ within ca. 10 minutes. The resultant suspension is stirred for 2 hours whilst cooling with ice. The precipitate is isolated, washed with water and acetone, and dried.

1.41 g of vinyl-ACA, containing 0.4% of 7-ADCA, are obtained.

EXAMPLE 6

Purification of Vinyl-ACA via Chromatography 10 g of vinyl-ACA, containing 1.0% 7-ADCA, are dissolved in 40 ml of water by adding aqueous ammonia to a pH of 8.5. The solution is placed in a column filled with 300 ml of HP-20 resin. Elution with water is carried out, and the eluate is collected in 25 ml fractions. The fractions with <1.0 HPLC area % of 7-ADCA are combined and vinyl-ACA is precipitated by adding conc. hydrochloric acid to pH 3.5. The precipitate is filtered off, washed with water and acetone, and dried. The resin is purified by washing with 80% methanol, and conditioned again with water.

6.2 g of vinyl-ACA, containing 0.1% (HPLC) of 7-ADCA, are obtained.

EXAMPLE 7

Purification of Vinyl-ACA via Chromatography 10 g of vinyl-ACA, containing 1.0% of 7-ADCA, obtained in fractions according to example 6, are dissolved by adding aqueous ammonia to a pH of 8.5. The solution is placed in a column filled with 350 ml of XAD-1600 resin and eluted with water. At a HPLC partition ratio of vinyl-ACA/7-ADCA of 1:1, the first fraction is taken out and discarded. At a 7-ADCA content in the eluate of ca. 1.0 HPLC area %, the second fraction is separated and used in a subsequent trial for dissolving the vinyl-ACA/7-ADCA starting mixture. The last fraction is acidified to a pH of 3.5 with conc. hydrochloric acid. The crystals obtained are filtered off, washed with water and acetone, and dried. The resin is purified by washing with 80% methanol and conditioned again with water.

7.6 g of vinyl-ACA, containing 0.2% (HPLC) 7-ADCA, are obtained.

What is claimed is:

1. A process for the depletion of a salt of 7-ADCA of formula

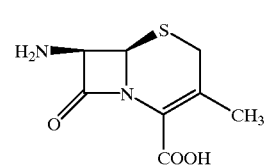

II from a mixture of a salt of 7-ADCA and a salt of vinyl-ACA of formula

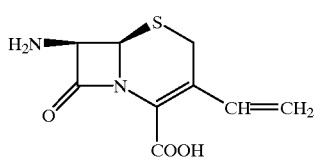

I wherein the process comprises:

a) producing a mixture of a salt of vinyl-ACA and a salt of 7-ADCA by addition of a salt forming agent to a compound of formula I and a compound of formula II, in a solvent in which the salt of 7-ADCA has a higher solubility than the salt of vinyl-ACA, wherein the solvent is selected from amides, ketones, alcohols, nitrites, esters, chlorinated hydrocarbons, water, or mixtures thereof, and wherein the salt forming agent is an inorganic base, an inorganic salt, anorganic salt or a nitrogen base; and b) subjecting said mixture to crystallization to obtain a precipitate of a salt of vinyl-ACA and a salt of 7-ADCA, in which the ratio of the salt of vinyl-ACA to the salt of 7-ADCA is greater than in the mixture.

2. A process according to claim 1, wherein said mixture of a salt of vinyl-ACA and a salt of 7-ADCA is a mixture of compounds of formulae

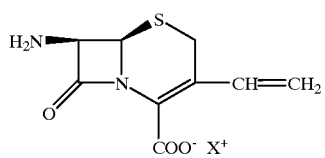

III

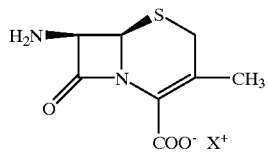

IV wherein X⁺ denotes Li+, Na+, K+ or a compound of formula

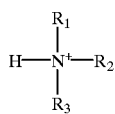

V wherein

R₁, R₂ and R₃ are the same or different and independently of one another denote hydrogen, alkyl, aryl, aralkyl, or cycloalkyl; or R₁ and R₂ together with the nitrogen atom form a 5- or 6-membered heterocycle containing one or several heteroatoms selected from the group consisting of N, S, and O and R₃ is as defined above.

3. A process according to claim 1, wherein the inorganic base is a hydroxide; the inorganic salt is an inorganic alkali salt; the organic salt is an alkali salt of a carboxylic acid; and the nitrogen base is a compound of formula

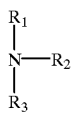

VI wherein

R₁, R₂ and R₃ are the same or different and independently of one another denote hydrogen, alkyl, aryl, aralkyl, or cycloalkyl; or R₁ and R₂ together with the nitrogen atom form a 5- or 6-membered heterocycle containing one or several heteroatoms selected from the group consisting of N, S, and O and R₃ is as defined above.

4. A compound of formula

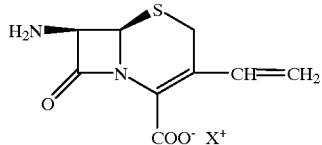

III wherein X⁺ is Li+, Na+, K+ or a compound of formula

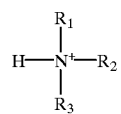

V wherein

R₁, R₂ and R₃ are the same or different and independently of one another denote hydrogen, alkyl, aryl, aralkyl, or cycloalkyl; or R₁ and R₂ together with the nitrogen atom form a 5- or 6-membered heterocycle containing one or several heteroatoms selected from the group consisting of N, S, and O and R₃ is as defined above, in crystalline form.

5. A dicyclohexylammonium salt of 7-amino-3-vinyl-cephalosporanic acid in crystalline form or a tert.octylammonium salt of 7-amino-3-vinyl-cephalosporanic acid in crystalline form or a N-benzyl-tert.butylammonium salt of 7-amino-3-vinyl-cephalosporanic acid in crystalline form or a 2-ethyl-1-hexylammonium salt of 7-amino-3-vinyl-cephalosporanic acid in crystalline form or a potassium salt of 7-amino-3vinyl-cephalosporanic acid in crystalline form.

6. A process according to claim 2 further comprising separation of the precipitate mixture and isolation of a compound of formula III.

7. A process according to claim 1, wherein the precipitate of the salt of vinyl-ACA and the salt of 7-ADCA is isolated and converted into vinyl-ACA of formula I and 7-ADCA of formula II by treatment with an acid.

8. A process according to claim 1, wherein the solvent is a mixture of water and a ketone or a mixture of water with an alcohol.

9. A process according to claim 1 wherein the solvent is water and acetone.

10. A process according to claim 1 wherein the solvent is water and ethanol.

11. A process according to claim 1 further comprising separation of the precipitate and isolation of a salt of vinyl-ACA.

12. A process according to claim 1 comprising
   c) resuspending or redissolving the precipitate in a solvent in which the salt of 7-ADCA has a higher solubility than the salt of vinyl-ACA, wherein the solvent is selected from amides, ketones, alcohols, nitrites, esters, chlorinated hydrocarbons, water, or mixtures thereof; and
   d) subjecting said precipitate to crystallization to obtain a second precipitate of a salt of vinyl-ACA and a salt of 7-ADCA, in which the ratio of the salt of vinyl-ACA to salt of 7-ADCA is greater than in said precipitate.

* * * * *

UNITED STATES PATENT AND TRADEMARK OFFICE
CERTIFICATE OF CORRECTION

PATENT NO. : 6,284,888 B1
DATED : September 4, 2001
INVENTOR(S) : Ludescher et al.

It is certified that error appears in the above-identified patent and that said Letters Patent is hereby corrected as shown below:

Column 12,
Line 43, should read: -- an inorganic base, an inorganic salt, an organic salt or a --

Column 14,
Line 44, should read: -- selected from amides, ketones, alcohols, nitriles, esters, --

Signed and Sealed this

Twenty-eighth Day of May, 2002

Attest:

*Attesting Officer*

JAMES E. ROGAN
*Director of the United States Patent and Trademark Office*